(12) United States Patent
Jung et al.

(10) Patent No.: US 11,913,932 B2
(45) Date of Patent: Feb. 27, 2024

(54) APPARATUS AND METHOD FOR MEASURING GAS CONCENTRATION

(71) Applicant: SAMSUNG ELECTRONICS CO., LTD., Suwon-si (KR)

(72) Inventors: Won Jong Jung, Seoul (KR); Kak Namkoong, Seoul (KR); Yeol Ho Lee, Anyang-si (KR); Joon Hyung Lee, Seongnam-si (KR); Ki Young Chang, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 909 days.

(21) Appl. No.: 16/830,690

(22) Filed: Mar. 26, 2020

(65) Prior Publication Data

US 2021/0055273 A1    Feb. 25, 2021

(30) Foreign Application Priority Data

Aug. 20, 2019 (KR) .................. 10-2019-0101665

(51) Int. Cl.
*G01N 27/12*    (2006.01)
*G01N 27/406*    (2006.01)
*G01N 33/00*    (2006.01)

(52) U.S. Cl.
CPC ......... *G01N 33/0067* (2013.01); *G01N 27/12* (2013.01); *G01N 27/122* (2013.01); *G01N 27/124* (2013.01); *G01N 27/127* (2013.01); *G01N 27/406* (2013.01); *G01N 27/4065* (2013.01); *G01N 33/0032* (2013.01)

(58) Field of Classification Search
CPC .... G01N 27/12; G01N 27/122; G01N 27/123; G01N 27/124; G01N 27/406; G01N 27/4065
See application file for complete search history.

(56) References Cited

U.S. PATENT DOCUMENTS 9,212,055 B2   12/2015 Zhou et al.
10,119,753 B2  11/2018 Jeong et al.
(Continued)

FOREIGN PATENT DOCUMENTS

CN    105637356 A    6/2016
CN    107064269 A    8/2017
(Continued)

OTHER PUBLICATIONS

Sang Joon Kim et at., "Innovative Nanosensor for Disease Diagnosis", Accounts of Chemical Research, Jul. 18, 2017, vol. 50, 2 pages.
(Continued)

*Primary Examiner* — Paul M. West
(74) *Attorney, Agent, or Firm* — Sughrue Mion, PLLC

(57) ABSTRACT

An apparatus for measuring a concentration of a target gas includes: a gas sensor including a sensing layer having an electric resistance that changes by an oxidation reaction or a reduction reaction between gas molecules and the sensing layer; and a processor configured to, in response to the target gas being introduced along with air into the gas sensor, monitor a change of the electric resistance of the sensing layer and determine the concentration of the target gas by analyzing a shape of the change of the electric resistance.

41 Claims, 14 Drawing Sheets

(56) References Cited

U.S. PATENT DOCUMENTS

| | | | |
|---|---|---|---|
| 10,228,338 B2 | 3/2019 | Petersen et al. | |
| 11,035,825 B2 | 6/2021 | Carbonelli et al. | |
| 2002/0154019 A1 | 10/2002 | Kimoto et al. | |
| 2006/0157348 A1 | 7/2006 | Inoue et al. | |
| 2008/0017507 A1* | 1/2008 | Ramamurthy | G01N 27/126 204/400 |
| 2010/0294024 A1 | 11/2010 | Kumar et al. | |
| 2013/0177995 A1 | 7/2013 | Chen et al. | |
| 2016/0084812 A1 | 3/2016 | Nishimoto et al. | |
| 2016/0223548 A1* | 8/2016 | Kizuka | G01N 33/0044 |
| 2016/0238554 A1 | 8/2016 | In et al. | |
| 2016/0334359 A1 | 11/2016 | Kim et al. | |
| 2017/0176403 A1 | 6/2017 | Matsumoto et al. | |
| 2017/0227484 A1 | 8/2017 | Petersen et al. | |
| 2019/0017981 A1 | 1/2019 | Dutta et al. | |
| 2019/0145929 A1* | 5/2019 | Carbonelli | G01N 33/0042 204/424 |
| 2019/0195823 A1* | 6/2019 | Chen | G01N 33/0039 |
| 2020/0200733 A1 | 6/2020 | Nolan et al. | |

FOREIGN PATENT DOCUMENTS

| | | |
|---|---|---|
| CN | 109781794 A | 5/2019 |
| JP | 2002-55068 A | 2/2002 |
| JP | 2006-208363 A | 8/2006 |
| JP | 2015-127644 A | 7/2015 |
| JP | 2016-65732 A | 4/2016 |
| JP | 2017-116295 A | 6/2017 |
| KR | 10-0869671 B1 | 11/2008 |
| KR | 10-2010-0025832 A | 3/2010 |
| WO | 2018017699 A1 | 1/2018 |

OTHER PUBLICATIONS

Sylvie Roussel et al. "Optimisation of electronic nose measurements. Part 1: Methodology of output feature selection" Journal of Food Engineering, vol. 37, No. 2, Aug. 1, 1998, (pp. 207-222).

A. Galdikas et al. "Response time based output of metal oxide gas sensors applied to evaluation of meat freshness with neural signal analysis" Sensors and Actuators B: Chemical, Elsevier BV, NL, vol. 69, No. 2, Oct. 25, 2000, (pp. 258-265).

Communication dated Nov. 13, 2020, issued by the European Patent Office in European Application No. 20174911.6.

Communication dated Oct. 31, 2023 by the China National Intellectual Property Administration in Chinese Patent Application No. 202010302671.9.

* cited by examiner

Sig_oxidation(t) = a+b*erf(c*t)

APPARATUS AND METHOD FOR MEASURING GAS CONCENTRATION

CROSS-REFERENCE TO RELATED APPLICATION(S)

This application claims priority from Korean Patent Application No. 10-2019-0101665, filed on Aug. 20, 2019, in the Korean Intellectual Property Office, the entire disclosure of which is incorporated herein by reference for all purposes.

BACKGROUND

1. Field

Apparatuses and methods of the present disclosure relate measuring a gas concentration.

2. Description of Related Art

Gas sensors for measuring the concentration of a specific gas generally use a method of measuring a gas concentration based on a change in electric resistance caused by gas molecules adsorbed/desorbed on the surface of the sensors.

In a common measurement environment, a target gas to be measured is mixed with air and is introduced into the gas sensor, in which case various gases contained in the air, other than the target gas to be measured, may be a factor in reducing accuracy of the gas sensor.

SUMMARY

Example embodiments provide an apparatus and method for measuring a gas concentration.

In accordance with an aspect of an example embodiment, an apparatus for measuring a concentration of a target gas includes a gas sensor including a sensing layer including an electric resistance that changes by an oxidation reaction or a reduction reaction between gas molecules and the sensing layer; and a processor configured to, in response to the target gas being introduced along with air into the gas sensor, monitor a change of the electric resistance of the sensing layer and determine the concentration of the target gas by analyzing a shape of the change of the electric resistance.

The processor may be further configured to approximate the change of the electric resistance as a sum of a first electric resistance change caused by the oxidation reaction and a second electric resistance change caused by the reduction reaction, and determine the concentration of the target gas based on the second electric resistance change.

The processor may be further configured to use a sigmoid function to approximate the change of the electric resistance.

The processor may be further configured to determine the concentration of the target gas by using a coefficient of a term of a predetermined function approximating the sum of the first electric resistance change and the second electric resistance change, the coefficient representing the second electric resistance change.

The processor may be further configured to determine the concentration of the target gas based on a predefined relationship between the coefficient and the concentration of the target gas.

The sensing layer may include at least one from among a metal oxide semiconductor (MOS), graphene, graphene oxide, a carbon nano tube (CNT), and a conductive polymer.

The sensing layer may include a nanostructure.

The nanostructure may include at least one from among a nanofiber structure, a nanotube structure, a nanoparticle structure, a nanosphere structure, and a nanobelt structure.

The sensing layer may include a metal catalyst for improving gas sensitivity and selectivity.

The gas sensor may further include an electric resistance measurer configured to measure the electric resistance of the sensing layer.

The gas sensor may further include a heater configured to control a reactivity of the sensing layer.

The apparatus may further include at least one from among a pressure sensor configured to measure a pressure exerted on the sensing layer or an ambient pressure around the sensing layer, a temperature sensor configured to measure a temperature of the sensing layer or an ambient temperature around the sensing layer, and a humidity sensor configured to measure an ambient humidity around the sensing layer.

The processor may be further configured to correct the determined concentration of the target gas based on at least one from among the measured pressure, the measured ambient pressure, the measured temperature, the measured ambient temperature, and the measured ambient humidity.

In accordance with an aspect of an example embodiment, an apparatus for measuring a concentration of a target gas includes a gas sensor including a sensing layer having an electric resistance that changes by an oxidation reaction or a reduction reaction between gas molecules and the sensing layer; and a processor configured to, in response to the target gas being introduced along with air into the gas sensor, monitor a change of the electric resistance of the sensing layer and determine the concentration of the target gas based on a slope of an electric resistance change during a predetermined time period after the target gas is introduced along with the air into the gas sensor.

The processor may be further configured to determine the concentration of the target gas based on a predefined relationship between the slope of the electric resistance change during the predetermined time period and the concentration of the target gas.

The predetermined time period may be a plateau time period.

The predetermined time period may begin at a time when the target gas is introduced along with the air into the gas sensor.

The sensing layer may include at least one from among a metal oxide semiconductor (MOS), graphene, graphene oxide, a carbon nano tube (CNT), and a conductive polymer.

The sensing layer may include a nanostructure.

The nanostructure may include at least one from among a nanofiber structure, a nanotube structure, a nanoparticle structure, a nanosphere structure, and a nanobelt structure.

The sensing layer may include a metal catalyst for improving gas sensitivity and selectivity.

The gas sensor may further include an electric resistance measurer configured to measure the electric resistance of the sensing layer.

The gas sensor may further include a heater configured to control a reactivity of the sensing layer.

The apparatus may further include at least one from among a pressure sensor configured to measure a pressure exerted on the sensing layer or an ambient pressure around the sensing layer, a temperature sensor configured to measure a temperature of the sensing layer or an ambient temperature around the sensing layer, and a humidity sensor configured to measure an ambient humidity around the sensing layer.

The processor may be further configured to correct the determined concentration of the target gas based on at least one from among the measured pressure, the measured ambient pressure, the measured temperature, the measured ambient temperature, and the measured ambient humidity.

In accordance with an aspect of an example embodiment, a method of measuring a concentration of a target gas by using a gas sensor having a sensing layer, wherein an electric resistance of the sensing layer changes by an oxidation reaction or a reduction reaction between gas molecules and the sensing layer, includes, in response to the target gas being introduced along with air into the gas sensor, monitoring a change of the electric resistance of the sensing layer; and determining the concentration of the target gas by analyzing a shape of the change of the electric resistance.

The determining of the concentration of the target gas may include approximating the change of the electric resistance as a sum of a first electric resistance change caused by the oxidation reaction and a second electric resistance change caused by the reduction reaction; and determining the concentration of the target gas based on the second electric resistance change.

The approximating of the change of the electric resistance may be performed using a sigmoid function.

The determining of the concentration of the target gas may include determining the concentration of the target gas by using a coefficient of a term of a predetermined function approximating the sum of the first electric resistance change and the second electric resistance change, the coefficient representing the second electric resistance change.

The determining of the concentration of the target gas may further include determining the concentration of the target gas based on a predefined relationship between the coefficient and the concentration of the target gas.

In accordance with an aspect of the disclosure, a method of measuring a concentration of a target gas by using a gas sensor including a sensing layer having an electric resistance that changes by an oxidation reaction or a reduction on between gas molecules and the sensing layer, includes, in response to the target gas being introduced along with the air into the gas sensor, monitoring a change of the electric resistance of the sensing layer; and determining the concentration of the target gas based on a slope of an electric resistance change during a predetermined time period after the target gas is introduced along with the air into the gas sensor.

The determining of the concentration of the target gas may include determining the concentration of the target gas based on a predefined relationship between the slope of the electric resistance change during the predetermined time period and the concentration of the target gas.

The predetermined time period may be a plateau time period.

The predetermined time period may begin at a time when the target gas is introduced along with air into the gas sensor.

In accordance with an aspect of the disclosure, a gas concentration sensor includes a sensing layer having an electric resistance that changes based on a concentration of a target gas in the gas concentration sensor; an electric resistance measurer configured to measure the electric resistance of the sensing layer at a predetermined time; a memory configured to store a predefined relationship between a change in the electric resistance of the sensing layer and the concentration of the target gas; and a processor configured to determine the concentration of the target gas based on the measured electric resistance and the stored predefined relationship.

The predefined relationship may include a first function defining electric resistance with respect to time, the first function including a first term having a coefficient; and a second function defining the concentration of the target gas with respect to the coefficient, wherein the processor is further configured to determine the coefficient of the first term in the first function based on the measured electric resistance and the predetermined time, and determine the concentration of the target gas based on the determined coefficient.

The first function may be a sum of the first term and a second term, the first term representing a first change in electric resistance caused by the target gas in the gas concentration sensor, and the second term representing a second change in electric resistance caused by an oxidation gas in the gas concentration sensor.

The predefined relationship may include a first function defining electric resistance with respect to time; and a second function defining the concentration of the target gas with respect to a slope of a region of the first function, wherein the processor is further configured to determine the slope of the region of the first function based on the measured electric resistance and the predetermined time, and determine the concentration of the target gas based on the determined slope.

The first function may be a sum of a first term and a second term, the first term representing a first change in electric resistance caused by the target gas in the gas concentration sensor, and the second term representing a second change in electric resistance caused by an oxidation gas in the gas concentration sensor.

The region of the first function may be a period of time over which the first function has a shape of a plateau.

The region of the first function may be a period of time beginning at a time when the target gas enters the gas concentration sensor.

BRIEF DESCRIPTION OF THE DRAWINGS

The above and other aspects, features, and advantages of example embodiments will be more apparent from the following description taken in conjunction with the accompanying drawings, in which.

DETAILED DESCRIPTION

Figure 1:
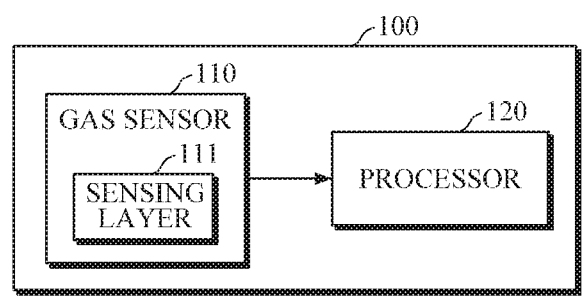
FIG. 1 is a block diagram illustrating an apparatus for measuring a gas concentration according to an example embodiment.

Hereinafter, embodiments of the disclosure will be described in detail with reference to the accompanying drawings. It should be noted that wherever possible, the same reference symbols and/or numerals refer to same parts even in different drawings. The relative size and depiction of elements in the drawings may be exaggerated for clarity, illustration, and convenience. In the following description, a detailed description of known functions and configurations incorporated herein will be omitted when such description may obscure the subject matter of the disclosure.

Process steps described herein may be performed differently from a specified order, unless a specified order is clearly stated in the context of the disclosure. That is, each step may be performed in a specified order, at substantially the same time as other steps, or in a reverse order.

Further, the terms used throughout this specification are defined in consideration of the functions according to example embodiments, and can be varied according to a purpose of a user or manager, or precedent and so on. Therefore, definitions of the terms should be made on the basis of the overall context.

It will be understood that, although the terms first, second, etc. may be used herein to describe various elements, these elements should not be limited by these terms. These terms are only used to distinguish one element from another. Any references to singular may include plural unless expressly stated otherwise. In the disclosure, it should be understood that the terms, such as 'including' or 'having,' etc., are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added. As used herein, expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, or all of a, b, and c.

Further, components that will be described in the specification are discriminated merely according to functions mainly performed by the components. That is, two or more components can be integrated into a single component. Furthermore, a single component can be separated into two or more components. Moreover, each component can additionally perform some or all of a function executed by another component in addition to the main function thereof. Some or all of the main function of each component can be carried out by another component. Each component may be implemented as hardware, software, or a combination of both.

Figure 2:
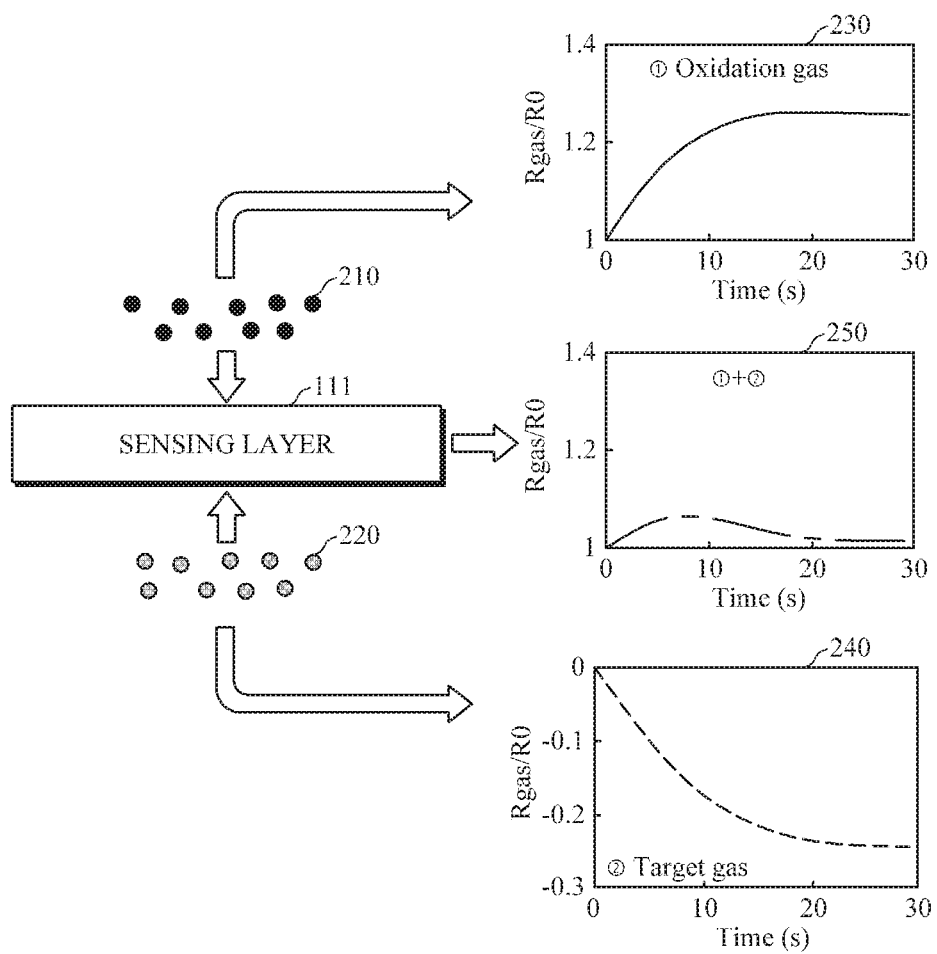
FIG. 2 is a diagram explaining a change in electric resistance of a sensing layer according to an example embodiment.

FIG. 1 is a block diagram illustrating an apparatus for measuring a gas concentration according to an example embodiment, and FIG. 2 is a diagram explaining a change in electric resistance of a sensing layer according to an example embodiment. FIG. 2 illustrates an example in which the sensing layer is formed as an n-type metal oxide semiconductor.

Referring to FIG. 1, the apparatus 100 for measuring a gas concentration (i.e., gas concentration sensor) includes a gas sensor 110 and a processor 120.

The gas sensor 110 may include a sensing layer 111, whose electric resistance changes by oxidation reaction or reduction reaction with gas molecules.

The sensing layer 111 may be made of a gas reactive material which is oxidized or reduced by gas molecules. In an embodiment, the gas reactive material may include a metal oxide semiconductor (MOS), graphene, graphene oxide, a carbon nano tube (CNT), a conductive polymer, or a combination thereof. Further, the gas reactive material may have a nanostructure, and may be arranged in 2D sheets. Here, the nanostructure may include a nanofiber structure, a nanotube structure, a nanoparticle structure, a nanosphere structure, a nanobelt structure, and the like.

In an embodiment, the sensing layer 111 may include a metal catalyst for improving gas sensitivity and selectivity. In this case, the metal catalyst may be dispersed in the gas reactive material by using a nano-size template.

For convenience of explanation, the following description will be given by using a MOS as an example of the gas reactive material.

The processor 120 may control the overall operation of the apparatus 100 for measuring a gas concentration, and may process various signals related to the operation of the apparatus 100 for measuring the gas concentration.

Once a target gas is introduced along with air into the gas sensor 110, the processor 120 may monitor a change in electric resistance of the sensing layer 111, and may determine a concentration of the target gas by analyzing the change in electric resistance of the sensing layer 111.

In an example embodiment, the processor 120 may determine the concentration of the target gas by analyzing a shape (e.g., an overall shape) of the change in electric resistance of the sensing layer 111 when the electric resistance is plotted with respect to time.

As illustrated in FIG. 2, once the target gas is introduced along with air into the gas sensor 110, an oxidation reaction between the sensing layer 111 and an oxidation gas 210 in the air and a reduction reaction between the sensing layer 111 and the target gas 220 may occur at the same time on the sensing layer 111, and the change in electric resistance of the sensing layer 111 may be determined by competitive reaction between the oxidation gas 210 and the target gas 220. Accordingly, the electric resistance change 250 of the sensing layer 111 may be expressed as a sum of an electric resistance change 230 caused by the oxidation reaction (i.e., a first electric resistance change), and an electric resistance change 240 caused by the reduction reaction (i.e., a second electric resistance change), as shown in Equation 1.

$$\text{Signal(resistance)} = \sum \text{Signal(gas}_i) = \sum \text{Signal(gas\_oxidation)} + \sum \text{Signal(target gas\_reduction)} \quad \text{[Equation 1]}$$

Herein, ΣSignal(gas_oxidation) denotes the electric resistance change caused by the oxidation gas, and ΣSignal (target gas_reduction) denotes an electric resistance change caused by the target gas.

In an example embodiment, by using a predetermined function (i.e., a first function), the processor 120 may approximate the electric resistance change of the sensing layer 111 as a sum of an electric resistance change caused by the oxidation reaction of the oxidation gas (e.g., oxygen) in the air, and an electric resistance change caused by the reduction reaction of the target gas. Here, the predetermined function may be a sigmoid function, including logistic function, hyperbolic function, arctangent function, error function, and the like, but is not limited thereto.

For example, the processor 120 may approximate the electric resistance change of the sensing layer 111 by using the following Equation 2.

$$f(t)=a+b\times\mathrm{erf}(c\times t)+d\times\mathrm{erf}(e\times t) \qquad \text{[Equation 2]}$$

Herein, d×erf(e×t) denotes the electric resistance change (i.e., a first change) caused by the reduction reaction of the target gas, b×erf(c×t) denotes the electric resistance change (i.e., a second change) caused by the oxidation reaction of the oxidation gas; erf denotes the error function; b and c denote properties of the oxidation gas in the air; and d and e denote properties of the target gas, in which a, b, and c may be determined during the process of generating a first concentration estimation equation (i.e., a second function) as will be described below.

The processor 120 may determine a concentration of the target gas based on the electric resistance change caused by the target gas.

For example, the processor 120 may determine the concentration of the target gas by using a coefficient of a term (i.e., a first term) of the predetermined function representing the electric resistance change caused by the target gas, and a first concentration estimation equation. For example, the term used may be the term d×erf(e×t) in Equation 2 above. In this case, the first concentration estimation equation may define a relationship between the coefficient of the term, representing the electric resistance change caused by the target gas, and the concentration of the target gas. Further, the first concentration estimation equation may be pre-obtained experimentally by regression analysis and may be stored in an internal or external database of the processor 120. For example, the processor 120 may determine the concentration of the target gas by using coefficient d of Equation 2 and the first concentration estimation equation (in this case, the first concentration estimation equation defines a relationship between the coefficient d and the concentration of the target gas), or may determine the concentration of the target gas by using both coefficients d and e of Equation 2 and the first concentration estimation equation (in this case, the first concentration estimation equation defines a relationship between the coefficients d and e and the concentration of the target gas).

While the above description is given of an example in which the apparatus 100 for measuring a gas concentration determines the concentration of one target gas, the apparatus 100 for measuring a gas concentration is not limited thereto. That is, the apparatus 100 for measuring a gas concentration may determine the concentration of two or more target gases, in which case an additional term representing an electric resistance change caused by an additional target gas may be further included in Equation 2.

In an embodiment, the processor 120 may determine the concentration of the target gas by analyzing a slope of the electric resistance change of the sensing layer 111 when the electric resistance is plotted with respect to time. For example, the processor 120 may determine the concentration of the target gas by using a slope of the electric resistance change during a predetermined phase and a second concentration estimation equation. Here, the predetermined phase may be a period of time, and the slope of the electric resistance change may be determined over the period of time. In this case, the predetermined phase may be a plateau time period (i.e., a period of time during which the electric resistance change is relatively small) or may be a phase between a time when the target gas is introduced along with air into the gas sensor 110 and a time when a predetermined period of time elapses (i.e., a predetermined period of time beginning at a time when the target gas is introduced along with air in the gas sensor 110). However, the predetermined phase is not limited thereto, and may be a phase between a first random time and a second random time. The second concentration estimation equation may define a relationship between the slope of the electric resistance change during the predetermined phase and the concentration of the target gas, and may be pre-obtained experimentally by regression analysis and may be stored in an internal or external database of the processor 120.

Figure 3A:
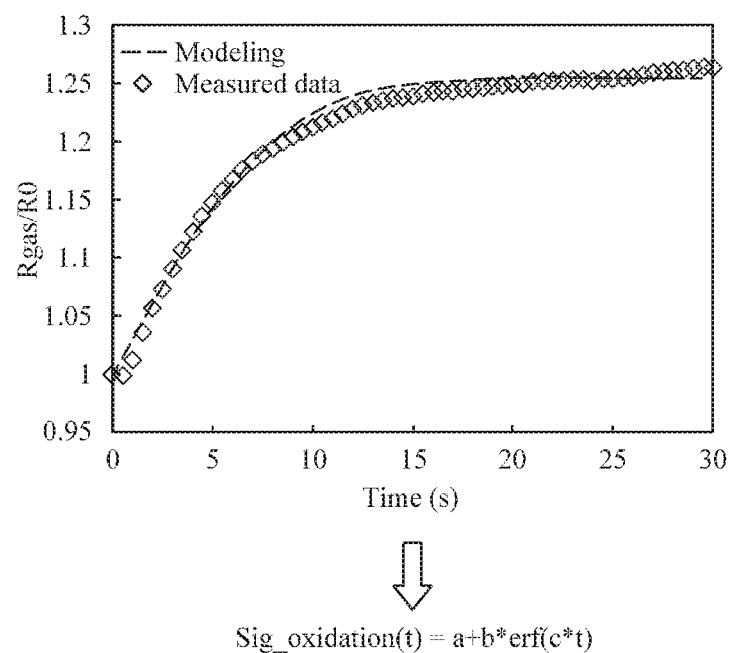
FIGS. 3A, 3B, and 3C are diagrams explaining generating a first concentration estimation equation according to an example embodiment.
Figure 3B:
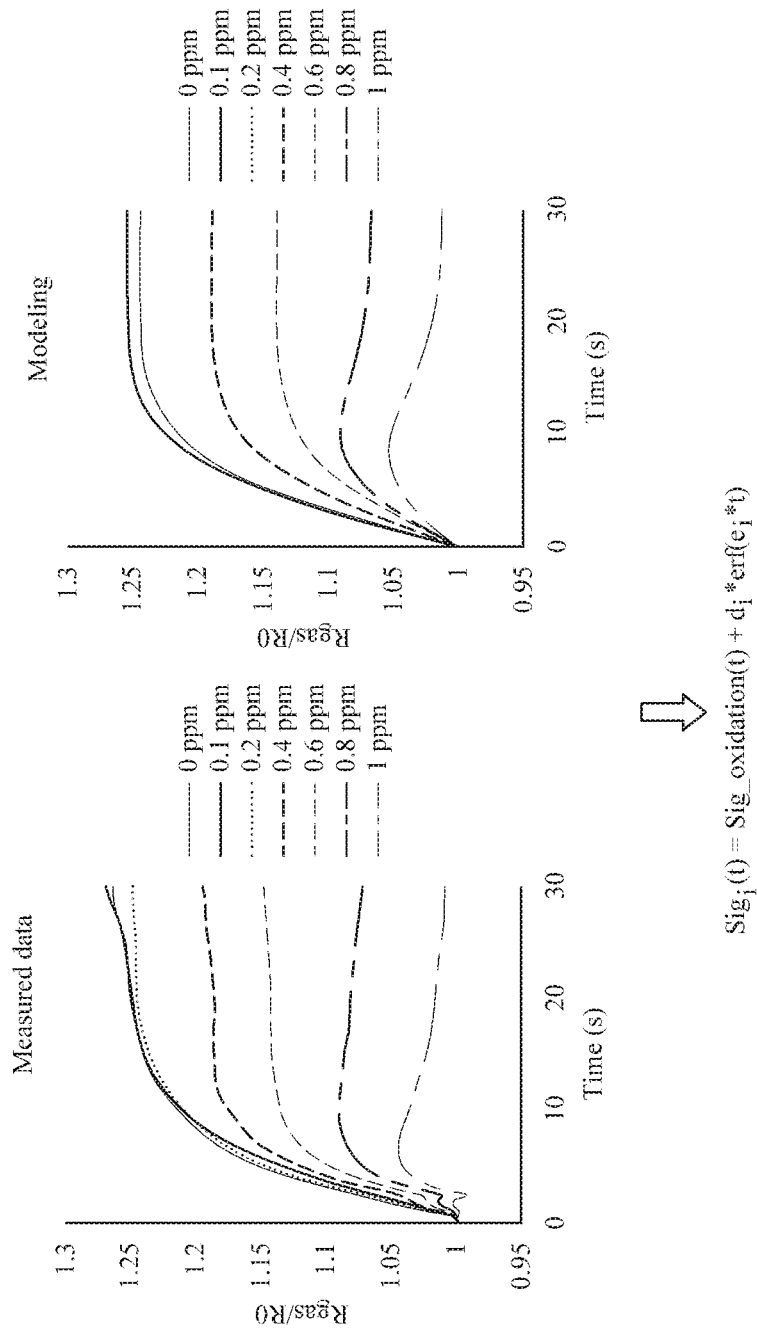
Figure 3C:
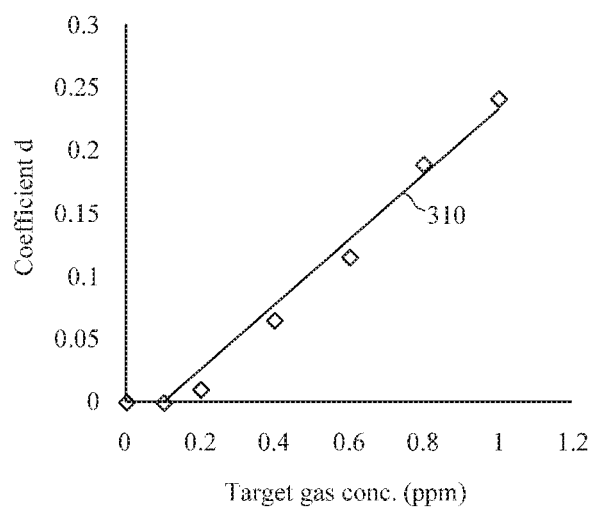

FIGS. 3A, 3B, and 3C are diagrams explaining generating a first concentration estimation equation according to an example embodiment. FIGS. 3A, 3B, and 3C illustrate an example in which a sensing layer is formed of an n-type metal oxide semiconductor.

Referring to FIG. 3A, once air is introduced into a gas sensor, the sensing layer 111 is oxidized by an oxidation gas in the air, such that electric resistance of the sensing layer 111 increases (alternately, in the case of a p-type metal oxide semiconductor, electric resistance is decreased by the oxidation reaction).

A change in electric resistance of the sensing layer 111 due to the oxidation reaction may be approximated by using a predetermined function, which may be represented by the following Equation 3.

$$\mathrm{Sig\_oxidation}=a+b\times\mathrm{erf}(c\times t) \qquad \text{[Equation 3]}$$

Herein, a, b, and c may be determined to fit the measured data taken during approximation of the electric resistance change, caused by the oxidation gas in the air, by using Equation 3, and the determined a, b, and c may be used for a, b, and c of Equation 2.

Referring to FIG. 3B, by introducing the target gas along with air into the gas sensor while varying the concentration of the target gas, the oxidation reaction of the oxidation gas in the air and the reduction reaction of the target gas may occur at the same time on the sensing layer 111, and the electric resistance change of the sensing layer 111 may be expressed as a sum of an amount of increase caused by the oxidation reaction and an amount of decrease caused by the reduction reaction (alternately, in the case of a p-type metal oxide semiconductor, a sum of an amount of decrease caused by the oxidation reaction and an amount of increase caused by the reduction reaction).

The overall electric resistance change of the sensing layer 111 may be approximated for each concentration of the target gas by using a predetermined function, which may be represented by the following Equation 4.

$$\mathrm{Sig}_i(t)=\mathrm{Sig\_oxidation}(t)+d_i*\mathrm{erf}(e_i*t) \qquad \text{[Equation 4]}$$

Herein, i denotes an index indicating the concentration of the target gas, and $d_i$ and $e_i$ may be determined during approximation of the electric resistance change, caused by the oxidation gas in the air and the target gas, for each concentration of the target gas by using Equation 4. The coefficients $d_i$ and $e_i$ may be determined to fit the measured data $\mathrm{Sig}_i(t)$ for each known concentration of target gas and for the known function Sig_oxidation(t).

Referring to FIG. 3C, it can be seen that there is a high correlation between coefficient d and the concentration of the target gas. Accordingly, by regression analysis of the coefficient d and the concentration of the target gas, the first concentration estimation equation 310 (shown as a line in FIG. 3C) may be generated. The predefined function and the first concentration estimation equation 310 may collectively be referred to as a predefined relationship between the coefficient of the term of the predefined function and the concentration of the target gas.

Figure 4A:
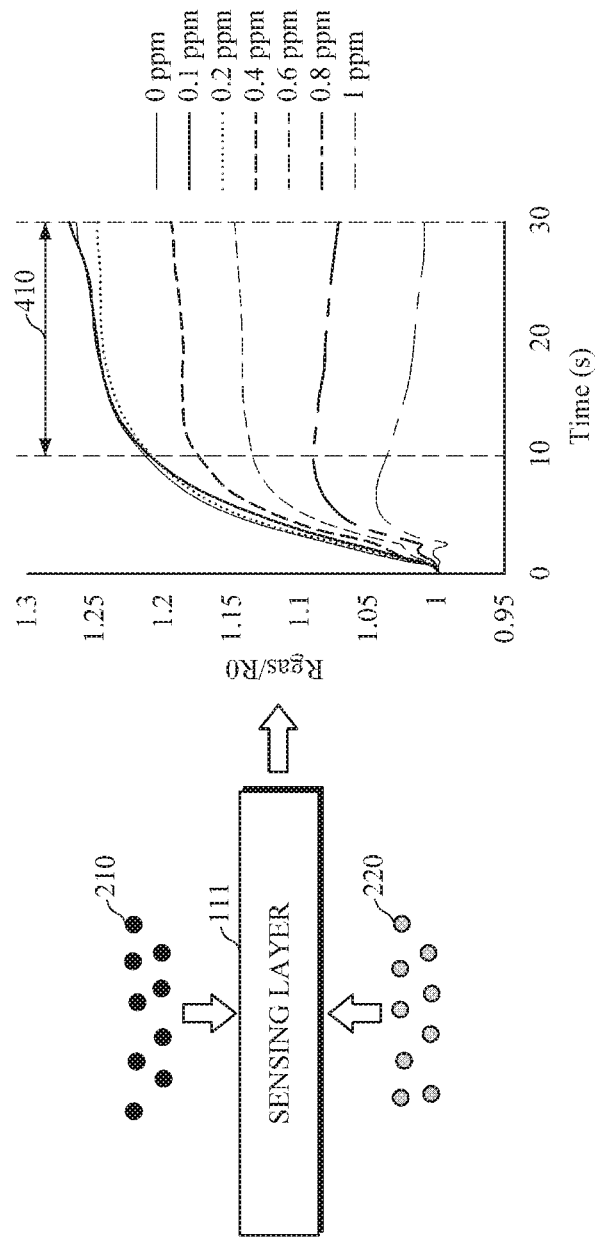
FIGS. 4A and 4B are diagrams explaining generating a second concentration estimation equation according to an example embodiment.
Figure 4B:
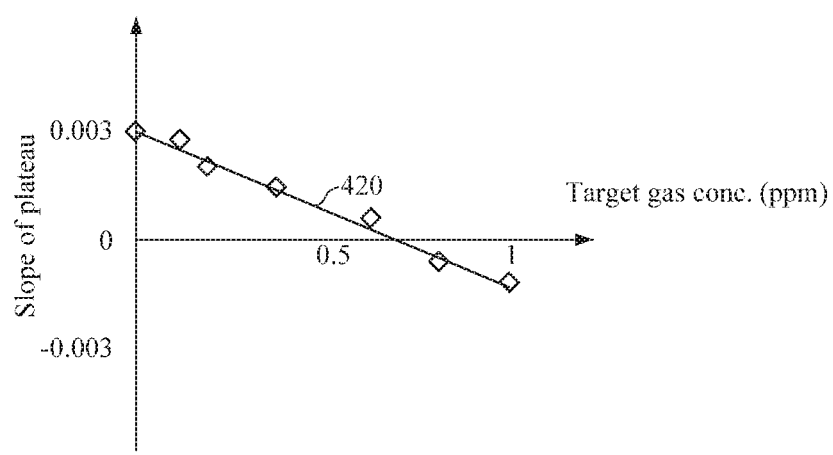

FIGS. 4A and 4B are diagrams explaining generating a second concentration estimation equation according to an example embodiment. FIGS. 4A and 4B illustrate an example in which a sensing layer is formed of an n-type metal oxide semiconductor.

Referring to FIG. 4A, by introducing the target gas 220 along with air into the gas sensor while varying the concentration of the target gas in known amounts, the oxidation reaction of the oxidation gas 210 in the air and the reduction reaction by the target gas 220 may occur at the same time on the sensing layer 111, and the electric resistance change of the sensing layer 111 may be expressed as a sum of an amount of increase caused by the oxidation reaction and an amount of decrease caused by the reduction reaction (alternately, in the case of a p-type metal oxide semiconductor, a sum of an amount of decrease caused by the oxidation reaction and an amount of increase caused by the reduction reaction).

By determining a plateau 410 of the electric resistance change of the sensing layer 111 for each concentration of the target gas, a slope of the plateau may be determined for each known concentration. The plateau 410 may be determined as a region corresponding to a period of time over which the electric resistance change has the shape of a plateau as shown, for example, in FIG. 4A.

Referring to FIG. 4B, it can be seen that there is a high correlation between the slope of the plateau 410 and the concentration of the target gas. Accordingly, by regression analysis of the slope of the plateau 410 and the concentration of the target gas, the second concentration estimation equation 420 (shown as a line in FIG. 4B) may be generated. The predefined function and the second concentration estimation equation 420 may collectively be referred to as a predefined relationship between the slope of the electric resistance change and the concentration of the target gas.

Figure 5A:
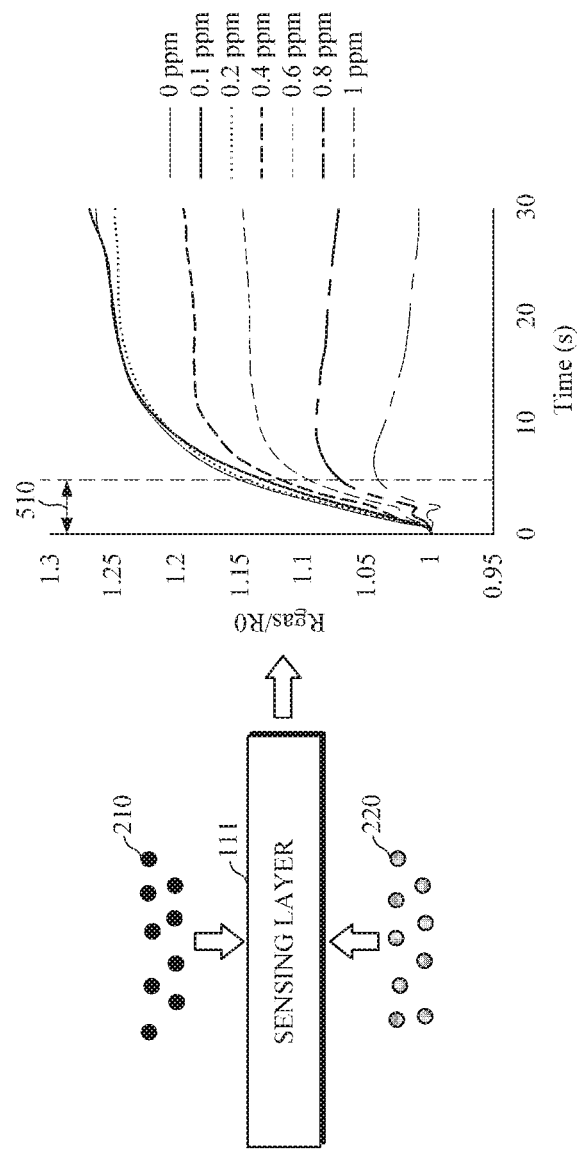
FIGS. 5A and 5B are diagrams explaining generating a second concentration estimation equation according to an example embodiment.
Figure 5B:
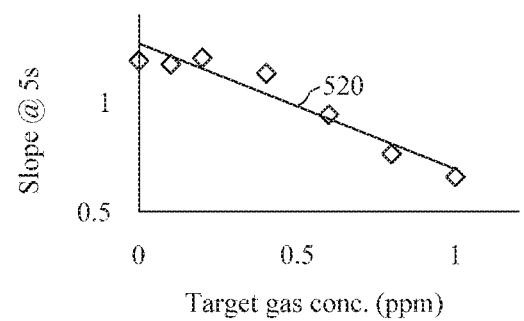

FIGS. 5A and 5B are diagrams explaining generating a second concentration estimation equation according to an example embodiment. FIGS. 5A to 5B illustrate an example in which a sensing layer is formed of an n-type metal oxide semiconductor.

Referring to FIG. 5A, by introducing the target gas 220 along with air into the gas sensor while varying the concentration of the target gas in known amounts, the oxidation reaction of the oxidation gas 210 in the air and the reduction reaction of the target gas 220 may occur at the same time on the sensing layer 111, and the electric resistance change of the sensing layer 111 may be expressed as a sum of an amount of increase caused by the oxidation reaction and an amount of decrease caused by the reduction reaction (alternately, in the case of a p-type metal oxide semiconductor, a sum of an amount of decrease caused by the oxidation reaction and an amount of increase caused by the reduction reaction).

A slope of the electric resistance change of the sensing layer 111 during a phase (i.e., a region) 510 between a time when the target gas 220 is introduced along with air into the gas sensor and a time when, for example, five seconds elapse may be determined for each concentration. In other words, the phase may be a predetermined period of time beginning at a time when the target gas 220 is introduced along with air into the gas sensor.

Referring to FIG. 5B, it can be seen that there is a high correlation between the concentration of the target gas 220 and the slope during the phase 510 between the time when the target gas 220 is introduced along with air into the gas sensor and the time when five seconds elapse. Accordingly, by regression analysis of the concentration of the target gas 220 and the slope during the phase 510 between the time when the target gas 220 is introduced along with air into the gas sensor and the time when five seconds elapse, the second concentration estimation equation 520 (shown as a line in FIG. 5B) may be generated.

Figure 6:
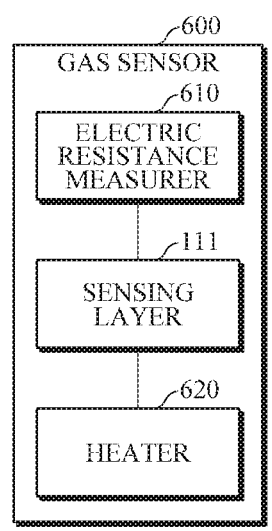
FIG. 6 is a block diagram illustrating a gas sensor according to an example embodiment.

FIG. 6 is a block diagram illustrating a gas sensor according to an example embodiment. The gas sensor 600 of FIG. 6 may be an example of the gas sensor 110 of FIG. 1.

Referring to FIG. 6, the gas sensor 600 includes the sensing layer 111 an electric resistance measurer 610, and a heater 620. Here, the sensing layer 111 is described above with reference to FIG. 1, such that a detailed description thereof will be omitted to avoid redundancy.

The electric resistance measurer 610 includes a plurality of electrodes, and may measure electric resistance of the sensing layer 111, for example, at a predetermined time or during a predetermined time period.

The heater 620 includes one or more electrodes, and may adjust temperature of the sensing layer 111 to control activity (i.e., reactivity) of the sensing layer 111.

Figure 7:
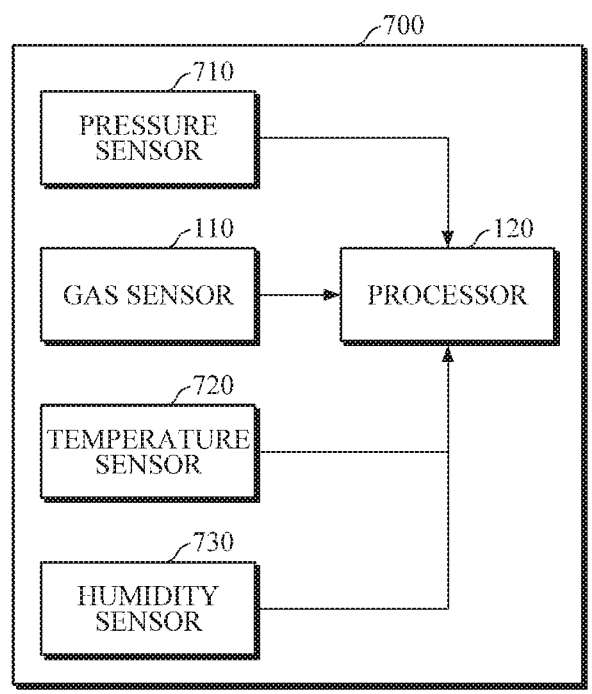
FIG. 7 is a block diagram illustrating an apparatus for measuring a gas concentration according to an example embodiment.

FIG. 7 is a block diagram illustrating an apparatus for measuring a gas concentration according to an example embodiment.

Referring to FIG. 7, the apparatus 700 for measuring a gas concentration includes the gas sensor 110, the processor 120, a pressure sensor 710, a temperature sensor 720, and a humidity sensor 730. Here, the gas sensor 110 and the processor 120 are described above with reference to FIG. 1, such that a detailed description thereof will be omitted to avoid redundancy.

The pressure sensor 710 may measure a pressure exerted on the sensing layer 111 of the gas sensor 110 or an ambient pressure around the sensing layer. For example, the pressure sensor 710 may include a barometric pressure sensor, an acceleration sensor, a strain gauge, a piezoelectric film, a load cell, radar, and the like, but is not limited thereto.

The temperature sensor 720 may measure a temperature of the sensing layer 111 of the gas sensor 110 or an ambient temperature around the sensing layer. The humidity sensor 730 may measure an ambient humidity around the sensing layer 111 of the gas sensor 110.

By analyzing the electric resistance change of the sensing layer 111 based on at least one of the pressure value measured by the pressure sensor 710 (measuring the pressure exerted on the sensing layer 111 or the ambient pressure around the sensing layer 111), the temperature value measured by the temperature sensor 720 (measuring the temperature of the sensing layer 111 or the ambient temperature around the sensing layer 111), and the humidity value measured by the humidity sensor 730 (measuring the ambient humidity around the sensing layer 111), the processor 120 may correct the determined concentration of the target gas. In this case, the processor 120 may use a concentration correction equation which defines a relationship between at least one of pressure, temperature, and humidity and the concentration of the target gas. The concentration correction equation may be obtained experimentally and may be stored in an internal or external database of the processor 120.

Figure 8:
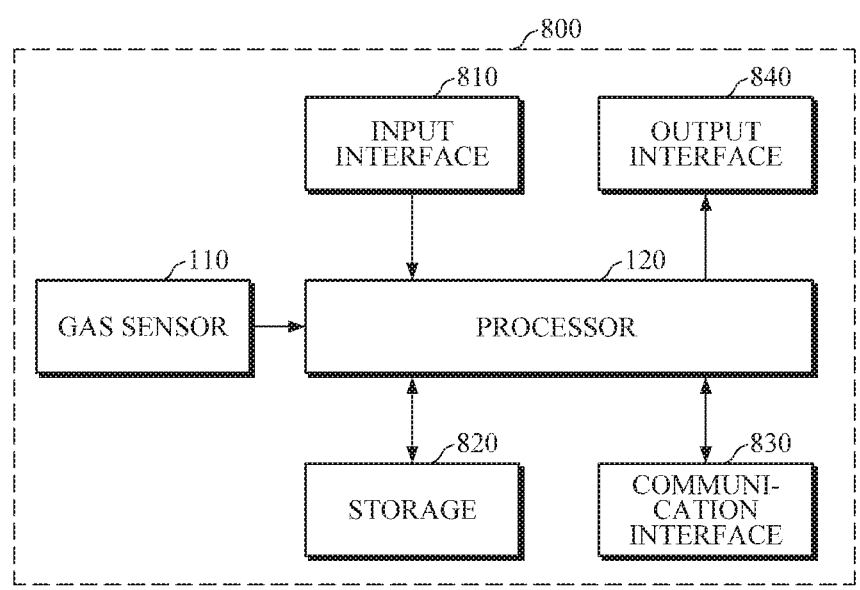
FIG. 8 is a block diagram illustrating an apparatus for measuring a gas concentration according to an example embodiment.

FIG. 8 is a block diagram illustrating an apparatus for measuring a gas concentration according to an example embodiment.

Referring to FIG. 8, the apparatus 800 for measuring a gas concentration includes the gas sensor 110, the processor 120, an input interface 810, a storage 820, a communication interface 830, and an output interface 840. Here, the gas sensor 110 and the processor 120 are described above with reference to FIGS. 1 to 7, such that a detailed description thereof will be omitted to avoid redundancy.

The input interface 810 may receive input of various operation signals from a user. In an embodiment, the input interface 810 may include a keypad, a dome switch, a touch pad (static pressure/capacitance), a jog wheel, a jog switch, a hardware (H/W) button, and the like. Particularly, the touch pad, which forms a layer structure with a display, may be called a touch screen.

The storage 820 may store programs or commands for operation of the apparatus 800 for measuring a gas concentration, and may store data input to the apparatus 800 for measuring a gas concentration, data measured and processed by the apparatus 800 for measuring a gas concentration, and the like. The storage 820 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like. Further, the apparatus 800 for measuring a gas concentration may operate an external storage medium, such as web storage and the like, which performs a storage function of the storage 820 on the Internet.

The communication interface 830 may communicate with an external device. For example, the communication interface 830 may transmit or receive, to or from the external device, the data input to and stored in the apparatus 800 for measuring a gas concentration, the data measured and processed by the apparatus 800 for measuring a gas concentration, and the like; or may transmit or receive, to or from the external device, various data useful for estimating bio-information.

In this case, the external device may be medical equipment using the data input to and stored in the apparatus 800 for measuring a gas concentration, the data measured and processed by the apparatus 800 for measuring a gas concentration, and the like, a printer to print out results, or a display to display the results. In addition, the external device may be a digital TV, a desktop computer, a cellular phone, a smartphone, a tablet PC, a laptop computer, a personal digital assistant (PDA), a portable multimedia player (PMP), a navigation device, an MP3 player, a digital camera, a wearable device, and the like, but is not limited thereto.

The communication interface 830 may communicate with an external device by using Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, 3G communication, 4G communication, 5G communication, and the like. However, these are merely examples and are not intended to be limiting.

The output interface 840 may output the data input to and stored in the apparatus 800 for measuring a gas concentration, the data measured and processed by the apparatus 800 for measuring a gas concentration, and the like. In an example embodiment, the output interface 840 may output the data input to and stored in the apparatus 800 for measuring a gas concentration, the data measured and processed by the apparatus 800 for measuring a gas concentration, and the like by using at least one of an acoustic method, a visual method, and a tactile method. To this end, the output interface 840 may include a display, a speaker, a vibrator, and the like.

Figure 9:
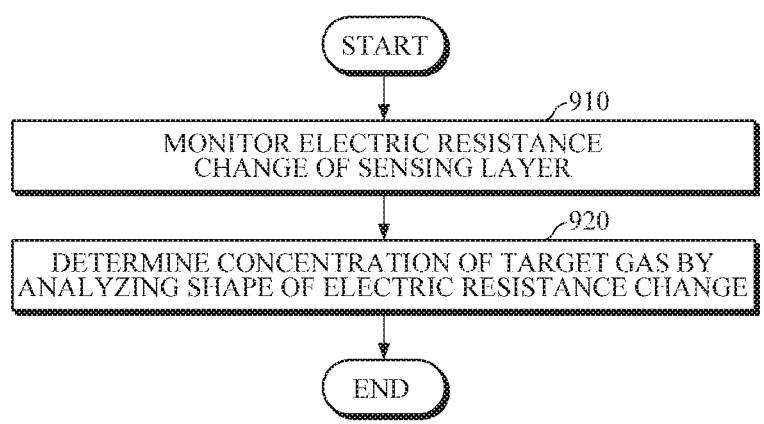
FIG. 9 is a flowchart illustrating a method of measuring a gas concentration according to an example embodiment.

FIG. 9 is a flowchart illustrating of a method of measuring a gas concentration of a target gas that has been introduced along with air into a gas sensor, according to an example embodiment. The method of measuring a gas concentration of FIG. 9 may be performed by the apparatuses 100, 700, and 800 for measuring a gas concentration described above with reference to FIGS. 1 to 8.

Referring to FIG. 9, once a target gas is introduced along with air into the gas sensor, the apparatus for measuring a gas concentration may monitor an electric resistance change of the sensing layer of the gas sensor in 910.

The apparatus for measuring a gas concentration may determine a concentration of the target gas by analyzing an overall shape of the electric resistance change of the sensing layer in 920.

As illustrated in FIG. 2, once the target gas is introduced along with air into the gas sensor, an oxidation reaction between a sensing layer and an oxidation gas in the air and a reduction reaction between the sensing layer and the target gas may occur at the same time on the sensing layer, and the electric resistance change of the sensing layer may be determined by competitive reaction between the oxidation gas and the target gas.

In an embodiment, the apparatus for measuring a gas concentration may approximate the electric resistance change of the sensing layer as a sum of an electric resistance change caused by the oxidation reaction of the oxidation gas in the air, and an electric resistance change caused by the reduction reaction of the target gas. Here, the predetermined function may be a sigmoid function, including logistic function, hyperbolic function, arctangent function, error function, and the like, but is not limited thereto. For example, the apparatus for measuring a gas concentration may approximate the electric resistance change of the sensing layer by using the above Equation 2.

The apparatus for measuring a gas concentration may determine the concentration of the target gas based on an electric resistance change caused by the target gas. For example, the apparatus for measuring a gas concentration may determine the concentration of the target gas by using a coefficient of a term (for example, the term d×erf(e×t) in Equation 2 above) of the predetermined function representing the electric resistance change caused by the target gas, and a first concentration estimation equation (for example, an equation representing the line 310 shown in FIG. 3C). In this case, the first concentration estimation equation may define a relationship between the coefficient of the term representing the electric resistance change caused by the target gas, and the concentration of the target gas. For example, the apparatus for measuring a gas concentration may determine the concentration of the target gas by using coefficient d of Equation 2 and the first concentration estimation equation (in this case, the first concentration estimation equation defines a relationship between the coefficient d and the concentration of the target gas), or may determine the concentration of the target gas by using both coefficients d and e of Equation 2 and the first concentration estimation equation (in this case, the first concentration estimation equation defines a relationship between the coefficients d and e and the concentration of the target gas).

Further, in an example embodiment, the apparatus for measuring a gas concentration may measure at least one of a pressure exerted on the sensing layer, an ambient pressure around the sensing layer, a temperature of the sensing layer, an ambient temperature around the sensing layer, and an ambient humidity around the sensing layer, and may correct the determined concentration of the target gas based on the at least one measured value. In this case, the apparatus for measuring a gas concentration may use a concentration correction equation which defines a relationship between the concentration of the target gas and at least one of pressure, temperature, and humidity.

Figure 10:
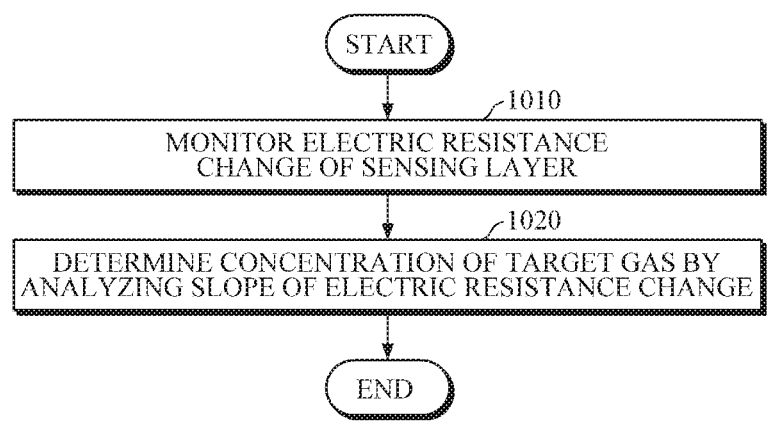
FIG. 10 is a flowchart illustrating a method of measuring a gas concentration according to an example embodiment.

FIG. 10 is a flowchart illustrating a method of measuring a gas concentration of a target gas that has been introduced along with air into a gas sensor, according to an example embodiment. The method of measuring a gas concentration of FIG. 10 may be performed by the apparatuses 100, 700, and 800 for measuring a gas concentration described above with reference to FIGS. 1 to 8.

Referring to FIG. 10, once the target gas is introduced along with air into the gas sensor, the apparatus for measuring a gas concentration may monitor an electric resistance change of the sensing layer of the gas sensor in 1010.

The apparatus for measuring a gas concentration may determine a concentration of the target gas by analyzing a slope of the electric resistance change of the sensing layer in 1020. For example, the apparatus for measuring a gas concentration may determine the concentration of the target gas by using a slope of the electric resistance change during a predetermined phase and a second concentration estimation equation (for example, an equation representing the line 420 shown in FIG. 4B). In this case, the predetermined phase may be any one of a plateau and a phase between a time when the target gas is introduced along with air into the gas sensor and a time when a predetermined period of time elapses. However, the predetermined phase is not limited thereto, and may be a phase between a first random time and a second random time. The second concentration estimation equation may define a relationship between the slope of the electric resistance change during the predetermined phase and the concentration of the target gas.

The example embodiments can be realized as a computer-readable code written on a computer-readable recording medium. The computer-readable recording medium may be any type of recording device in which data is stored in a computer-readable manner.

Examples of the computer-readable recording medium include a ROM, a RAM, a CD-ROM, a magnetic tape, a floppy disc, an optical data storage, and a carrier wave (e.g., data transmission through the Internet). The computer-readable recording medium can be distributed over a plurality of computer systems connected to a network so that a computer-readable code is written thereto and executed therefrom in a decentralized manner. Functional programs, codes, and code segments needed for realizing embodiments can be deduced by one of ordinary skill in the art.

While example embodiments have been described, it will be understood to those skilled in the art that various changes and modifications can be made without changing technical ideas and essential features of the present disclosure. Thus, it is clear that the above-described example embodiments are illustrative in all aspects and are not intended to limit the present disclosure.

What is claimed is:

1. An apparatus for measuring a concentration of a target gas, the apparatus comprising:
    a gas sensor comprising a sensing layer having an electric resistance that changes by an oxidation reaction or a reduction reaction between gas molecules and the sensing layer; and
    a processor configured to, in response to the target gas being introduced along with air into the gas sensor, monitor a change of the electric resistance of the sensing layer and determine the concentration of the target gas by analyzing a shape of the change of the electric resistance,
    wherein the processor is further configured to approximate the change of the electric resistance as a sum of a first electric resistance change caused by the oxidation reaction and a second electric resistance change caused by the reduction reaction.

2. The apparatus of claim 1, wherein the processor is further configured to determine the concentration of the target gas based on the second electric resistance change.

3. The apparatus of claim 2, wherein the processor is further configured to use a sigmoid function to approximate the change of the electric resistance.

4. The apparatus of claim 2, wherein the processor is further configured to determine the concentration of the target gas by using a coefficient of a term of a predetermined function approximating the sum of the first electric resistance change and the second electric resistance change, the coefficient representing the second electric resistance change.

5. The apparatus of claim 4, wherein the processor is further configured to determine the concentration of the target gas based on a predefined relationship between the coefficient and the concentration of the target gas.

6. The apparatus of claim 1, wherein the sensing layer comprises at least one of a metal oxide semiconductor (MOS), graphene, graphene oxide, a carbon nano tube (CNT), and a conductive polymer.

7. The apparatus of claim 1, wherein the sensing layer comprises a nanostructure.

8. The apparatus of claim 7, wherein the nanostructure comprises at least one of a nanofiber structure, a nanotube structure, a nanoparticle structure, a nanosphere structure, and a nanobelt structure.

9. The apparatus of claim 1, wherein the sensing layer comprises a metal catalyst for improving gas sensitivity and selectivity.

10. The apparatus of claim 1, wherein the gas sensor further comprises an electric resistance measurer configured to measure the electric resistance of the sensing layer.

11. The apparatus of claim 1, wherein the gas sensor further comprises a heater configured to control a reactivity of the sensing layer.

12. The apparatus of claim 1, further comprising at least one of a pressure sensor configured to measure a pressure exerted on the sensing layer or an ambient pressure around the sensing layer, a temperature sensor configured to measure a temperature of the sensing layer or an ambient temperature around the sensing layer, and a humidity sensor configured to measure an ambient humidity around the sensing layer.

13. The apparatus of claim 12, wherein the processor is further configured to correct the determined concentration of the target gas based on at least one of the measured pressure, the measured ambient pressure, the measured temperature, the measured ambient temperature, and the measured ambient humidity.

14. An apparatus for measuring a concentration of a target gas, the apparatus comprising:
a gas sensor comprising a sensing layer having an electric resistance that changes by an oxidation reaction or a reduction reaction between gas molecules and the sensing layer; and
a processor configured to, in response to the target gas being introduced along with air into the gas sensor, monitor a change of the electric resistance of the sensing layer and determine the concentration of the target gas based on a slope of an electric resistance change during a predetermined time period after the target gas is introduced along with the air into the gas sensor,
wherein the processor is further configured to approximate the change of the electric resistance as a sum of a first electric resistance change caused by the oxidation reaction and a second electric resistance change caused by the reduction reaction.

15. The apparatus of claim 14, wherein the processor is further configured to determine the concentration of the target gas based on a predefined relationship between the slope of the electric resistance change during the predetermined time period and the concentration of the target gas.

16. The apparatus of claim 15, wherein the predetermined time period is a plateau time period.

17. The apparatus of claim 15, wherein the predetermined time period begins at a time when the target gas is introduced along with the air into the gas sensor.

18. The apparatus of claim 14, wherein the sensing layer comprises at least one of among a metal oxide semiconductor (MOS), graphene, graphene oxide, a carbon nano tube (CNT), and a conductive polymer.

19. The apparatus of claim 14, wherein the sensing layer comprises a nanostructure.

20. The apparatus of claim 19, wherein the nanostructure comprises at least one of a nanofiber structure, a nanotube structure, a nanoparticle structure, a nanosphere structure, and a nanobelt structure.

21. The apparatus of claim 14, wherein the sensing layer comprises a metal catalyst for improving gas sensitivity and selectivity.

22. The apparatus of claim 14, wherein the gas sensor further comprises an electric resistance measurer configured to measure the electric resistance of the sensing layer.

23. The apparatus of claim 14, wherein the gas sensor further comprises a heater configured to control a reactivity of the sensing layer.

24. The apparatus of claim 14, further comprising at least one of a pressure sensor configured to measure a pressure exerted on the sensing layer or an ambient pressure around the sensing layer, a temperature sensor configured to measure a temperature of the sensing layer or an ambient temperature around the sensing layer, and a humidity sensor configured to measure an ambient humidity around the sensing layer.

25. The apparatus of claim 24, wherein the processor is further configured to correct the determined concentration of the target gas based on at least one of the measured pressure, the measured ambient pressure, the measured temperature, the measured ambient temperature, and the measured ambient humidity.

26. A method of measuring a concentration of a target gas by using a gas sensor comprising a sensing layer having an electric resistance that changes by an oxidation reaction or a reduction reaction between gas molecules and the sensing layer, the method comprising:
in response to the target gas being introduced along with air into the gas sensor, monitoring a change of the electric resistance of the sensing layer; and
determining the concentration of the target gas by analyzing a shape of the change of the electric resistance,
wherein the determining of the concentration of the target gas comprises approximating the change of the electric resistance as a sum of a first electric resistance change caused by the oxidation reaction and a second electric resistance change caused by the reduction reaction.

27. The method of claim 26, wherein the determining of the concentration of the target gas further comprises:
determining the concentration of the target gas based on the second electric resistance change.

28. The method of claim 27, wherein the approximating of the change of the electric resistance is performed using a sigmoid function.

29. The method of claim 27, wherein the determining of the concentration of the target gas comprises determining the concentration of the target gas by using a coefficient of a term of a predetermined function approximating the sum of the first electric resistance change and the second electric resistance change, the coefficient representing the second electric resistance change.

30. The method of claim 29, wherein the determining of the concentration of the target gas further comprises determining the concentration of the target gas based on a predefined relationship between the coefficient and the concentration of the target gas.

31. A method of measuring a concentration of a target gas by using a gas sensor comprising a sensing layer having an electric resistance that changes by an oxidation reaction or a reduction reaction between gas molecules and the sensing layer, the method comprising:
in response to the target gas being introduced along with the air into the gas sensor, monitoring a change of the electric resistance of the sensing layer; and
determining the concentration of the target gas based on a slope of an electric resistance change during a predetermined time period after the target gas is introduced along with the air into the gas sensor,
wherein the determining of the concentration of the target gas comprises approximating the change of the electric resistance as a sum of a first electric resistance change caused by the oxidation reaction and a second electric resistance change caused by the reduction reaction.

32. The method of claim 31, wherein the determining of the concentration of the target gas comprises determining the concentration of the target gas based on a predefined relationship between the slope of the electric resistance change during the predetermined time period and the concentration of the target gas.

33. The method of claim 31, wherein the predetermined time period is a plateau time period.

34. The method of claim 31, wherein the predetermined time period begins at a time when the target gas is introduced along with air into the gas sensor.

35. A gas concentration sensor comprising:
a sensing layer having an electric resistance that changes based on a concentration of a target gas in the gas concentration sensor;

an electric resistance measurer configured to measure the electric resistance of the sensing layer at a predetermined time;

a memory configured to store a predefined relationship between a change in the electric resistance of the sensing layer and the concentration of the target gas; and a processor configured to determine the concentration of the target gas based on the measured electric resistance and the stored predefined relationship, wherein the processor is further configured to approximate the change of the electric resistance as a sum of a first electric resistance change caused by an oxidation reaction and a second electric resistance change caused by a reduction reaction.

36. The gas concentration sensor of claim 35, wherein the predefined relationship comprises:

a first function defining electric resistance with respect to time, the first function including a first term having a coefficient; and a second function defining the concentration of the target gas with respect to the coefficient, and wherein the processor is further configured to determine the coefficient of the first term in the first function based on the measured electric resistance and the predetermined time, and determine the concentration of the target gas based on the determined coefficient.

37. The gas concentration sensor of claim 36, wherein the first function is a sum of the first term and a second term, the first term representing a first change in electric resistance caused by the target gas in the gas concentration sensor, and the second term representing a second change in electric resistance caused by an oxidation gas in the gas concentration sensor.

38. The gas concentration sensor of claim 35, wherein the predefined relationship comprises:

a first function defining electric resistance with respect to time; and a second function defining the concentration of the target gas with respect to a slope of a region of the first function, and wherein the processor is further configured to determine the slope of the region of the first function based on the measured electric resistance and the predetermined time, and determine the concentration of the target gas based on the determined slope.

39. The gas concentration sensor of claim 38, wherein the first function is a sum of a first term and a second term, the first term representing a first change in electric resistance caused by the target gas in the gas concentration sensor, and the second term representing a second change in electric resistance caused by an oxidation gas in the gas concentration sensor.

40. The gas concentration sensor of claim 38, wherein the region of the first function is a period of time over which the first function has a shape of a plateau.

41. The gas concentration sensor of claim 38, wherein the region of the first function is a period of time beginning at a time when the target gas enters the gas concentration sensor.

* * * * *